(12) United States Patent
Imran et al.

(10) Patent No.: US 9,107,993 B2
(45) Date of Patent: Aug. 18, 2015

(54) MYOCARDIAL DRUG DELIVERY APPARATUS AND METHOD

(71) Applicants: Mir Imran, Los Altos Hills, CA (US); Paul Spehr, San Antonio, TX (US); Philip F. Morgan, San Antonio, TX (US); Elmar Fischer, Boerne, TX (US)

(72) Inventors: Mir Imran, Los Altos Hills, CA (US); Paul Spehr, San Antonio, TX (US); Philip F. Morgan, San Antonio, TX (US); Elmar Fischer, Boerne, TX (US)

(73) Assignee: INCUBE LABS, LLC, San Jose, CA (US)

(*) Notice: Subject to any disclaimer, the term of this patent is extended or adjusted under 35 U.S.C. 154(b) by 0 days.

(21) Appl. No.: 13/681,825

(22) Filed: Nov. 20, 2012

(65) Prior Publication Data

US 2013/0218124 A1 Aug. 22, 2013

Related U.S. Application Data

(60) Provisional application No. 61/629,599, filed on Nov. 21, 2011, provisional application No. 61/629,609, filed on Nov. 21, 2011.

(51) Int. Cl.
*A61N 1/00* (2006.01)
*A61B 18/18* (2006.01)
*A61M 5/14* (2006.01)
*A61M 37/00* (2006.01)
*A61N 1/39* (2006.01)
(Continued)

(52) U.S. Cl.
CPC .............. *A61M 5/14* (2013.01); *A61M 37/0069* (2013.01); *A61B 5/0422* (2013.01); *A61B 5/4839* (2013.01); *A61B 5/6852* (2013.01); *A61B 5/6869* (2013.01); *A61N 1/362* (2013.01); *A61N 1/3962* (2013.01)

(58) Field of Classification Search
USPC ............................................ 607/120; 606/41
See application file for complete search history.

(56) References Cited

U.S. PATENT DOCUMENTS 5,170,785 A 12/1992 Heinz et al.
5,181,511 A 1/1993 Nickolls et al.
(Continued)

FOREIGN PATENT DOCUMENTS

EP 0830876 A2 3/1998
WO WO 97/24983 A2 7/1997
(Continued)

OTHER PUBLICATIONS

U.S. Appl. No. 13/827,468, filed Mar. 14, 2013, Imran et al.
(Continued)

*Primary Examiner* — Nicole F Lavert
(74) *Attorney, Agent, or Firm* — Wilson Sonsini Goodrich & Rosati

(57) ABSTRACT

Embodiments provide apparatus and methods for delivering solid form drug (SFD) to various locations in the body. In one embodiment, the invention provides an apparatus for treatment of arrhythmia comprising a drug delivery member (DDM) coupled to a drug storage device (DSD). The DSD is configured to store and advance SFD (e.g., drug pellets) through the DDM to a target tissue site (TTS) in or on the heart. A drug advancement member may be used to advance the SFD through the DSD. A capture chamber (CC) may be coupled to the DDM. and is configured to be positioned on a heart surface and allow SFD to dissolve to deliver a drug solution to the heart. The DSD can be implanted subcutaneously e.g., in the pectoral area. Embodiments of the apparatus can be used to store and deliver SFD to the heart or other TTS over an extended period of years.

41 Claims, 10 Drawing Sheets

| (51) | Int. Cl. | |
|---|---|---|
| | A61N 1/362 | (2006.01) |
| | A61B 5/00 | (2006.01) |
| | A61B 5/042 | (2006.01) |

(56) References Cited

U.S. PATENT DOCUMENTS

| 6,023,638 | A | 2/2000 | Swanson |
|---|---|---|---|
| 6,295,476 | B1 | 9/2001 | Schaenzer |
| 6,466,811 | B1 | 10/2002 | Hassett |
| 7,272,438 | B2 | 9/2007 | Kroll et al. |
| 7,308,310 | B1 | 12/2007 | Levine et al. |
| 2003/0199956 | A1 | 10/2003 | Struble et al. |
| 2004/0019366 | A1 | 1/2004 | Rottenberg et al. |
| 2004/0215253 | A1 | 10/2004 | Weinberg |
| 2005/0090872 | A1 | 4/2005 | Deno et al. |
| 2005/0215991 | A1* | 9/2005 | Altman et al. .................. 606/41 |
| 2005/0288724 | A1 | 12/2005 | Begemann et al. |
| 2006/0149331 | A1 | 7/2006 | Mann et al. |
| 2006/0161211 | A1 | 7/2006 | Thompson et al. |
| 2006/0206157 | A1 | 9/2006 | Hoijer |
| 2007/0239248 | A1 | 10/2007 | Hastings et al. |
| 2007/0275035 | A1 | 11/2007 | Herman et al. |
| 2008/0021505 | A1 | 1/2008 | Hastings et al. |
| 2008/0071338 | A1 | 3/2008 | Jiang et al. |
| 2008/0234773 | A1 | 9/2008 | Ni et al. |
| 2009/0149833 | A1 | 6/2009 | Cima et al. |
| 2010/0114309 | A1* | 5/2010 | de Juan, Jr. et al. ......... 623/6.39 |
| 2010/0268291 | A1 | 10/2010 | Imran |
| 2010/0268295 | A1 | 10/2010 | Imran et al. |
| 2010/0330149 | A1 | 12/2010 | Daniel et al. |

FOREIGN PATENT DOCUMENTS

| WO | WO 2010/107507 A1 | 9/2010 |
|---|---|---|
| WO | WO 2011/106502 A2 | 9/2011 |
| WO | WO 2012/047931 A1 | 4/2012 |

OTHER PUBLICATIONS

European search report and opinion dated Sep. 11, 2012 for EP Application No. 10767635.5.
International search report and written opinion dated Mar. 4, 2013 for PCT/US2012/066156.
International search report and written opinion dated Nov. 29, 2010 for PCT/US2010/031748.
Office action dated May 25, 2011 for U.S. Appl. No. 12/427,733.
Office action dated Jun. 29, 2012 for U.S. Appl. No. 12/757,865.
Office action dated Jul. 12, 2012 for U.S. Appl. No. 12/427,733.
Office action dated Nov. 23, 2011 for U.S. Appl. No. 12/757,865.
Amano, Y. The cerebrospinal fluid production rate in the experimentally induced edematous brain and influences of dexamethasone upon it. Nagoya J Med Sci. Mar. 1969;31(3):427-41.
International search report and written opinion dated Dec. 5, 2014 for PCT/US2014/025018.
European search report and search opinion dated Mar. 3, 2015 for EP Application No. 12852050.9.

* cited by examiner

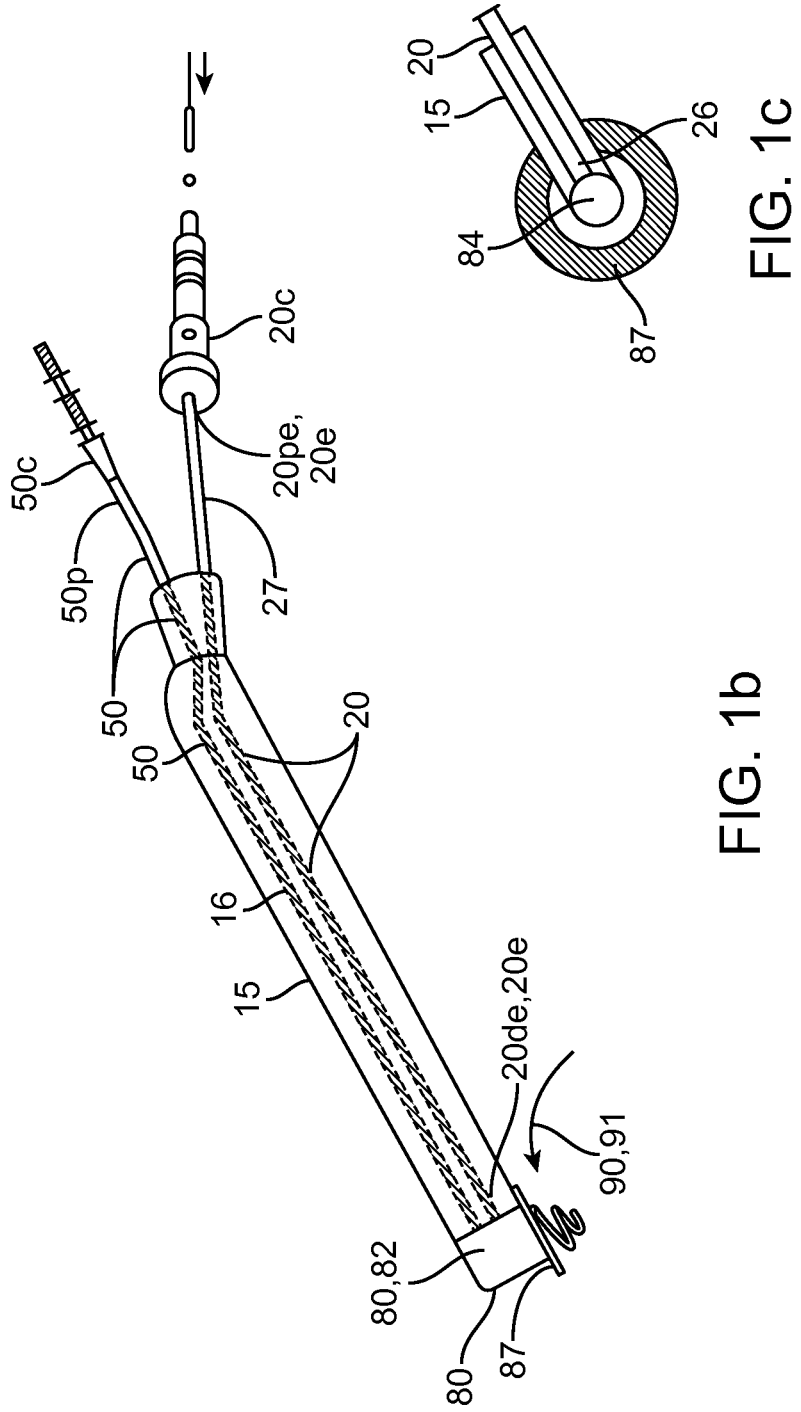

MYOCARDIAL DRUG DELIVERY APPARATUS AND METHOD

CROSS-REFERENCE

This application claims the benefit of priority of Provisional Application Nos. 61/629,599 and 61/629,609 both entitled "Myocardial Drug Delivery Apparatus for Treatment of Cardiac Rhythm Disorders" and both filed Nov. 21, 2011; which are fully incorporated by reference herein for all purposes.

BACKGROUND OF THE INVENTION

Field of the Invention

Embodiments of the invention relate to drug delivery devices and methods of use thereof. More specifically, embodiments of the invention relate to a drug delivery apparatus for the delivery of solid form drugs and other therapeutic agents. Still more specifically embodiments of the invention relate to a drug delivery apparatus for the delivery of solid form drugs to the myocardium for the treatment of atrial fibrillation.

The heart has four chambers, the right and left atria and the right and left ventricles. The atria serve as primer pumps to the ventricles which in turn pump blood to the lungs (the right ventricle) or the aorta and the remainder of the body (the left ventricle). The heart is essentially and electromechanical pump, which contracts and pumps blood by means of a wave of depolarization that spreads from the atria to the ventricles in a timed fashion through a series of conduction pathways. Cardiac arrhythmia is a condition afflicting the heart and is characterized by abnormal conduction patterns in cardiac tissue. These abnormal conduction patterns can in turn affect the pumping efficiency in one of more chambers of the heart. It can occur in either the atria, ventricles or both. Particular types of atrial arrhythmia can cause a condition known as atrial fibrillation (AF) in which the pumping efficiency of the atria are compromised. Instead of contracting in a coordinated fashion, the left or right atrial flutter with little or no pumping efficiency.

During an episode of AF, the normal electrical impulses that are generated by the sino-atrial node (the SA node), the natural pacemaker of the heart are overwhelmed by disorganized electrical impulses, known as ectopic foci that may originate in the atria or pulmonary veins, leading to conduction of irregular impulses to the atria and the ventricles. This can result in an irregular heartbeat, known as an arrhythmia which may occur in episodes lasting from minutes to weeks, or years. Left unchecked, AF often progresses to become a chronic condition.

Atrial fibrillation is often asymptomatic, and while not immediately life-threatening, may result in palpitations, fainting, chest pain (angina), or congestive heart failure. Patients with AF have a significantly increased risk of stroke and pulmonary embolism due to the tendency of blood to pool and form clots or emboli in the poorly contracting atria which are then sent to the lungs in the case of the right atria causing pulmonary embolism, or the brain causing stroke.

Atrial fibrillation may be treated with medications, implanted ventricular defibrillators or surgical procedures. The current medications used either slow the heart rate or revert the heart rhythm back to normal. However patients must remain on medication for life and many patients cannot be successfully treated with medication. Implanted ventricular defibrillators may be used to deliver a series of high voltage electric shocks to convert AF to a normal heart rhythm in a technique known as synchronized electrical cardioversion. However, these shocks are extremely painful and may cause the patient to pass or literally be knocked to the ground from the shock. Surgical and catheter-based therapies may also be used to ablate or destroy portions of the atria and pulmonary veins containing the ectopic and other foci responsible for the generation of arrhythmias causing AF; however, these require open heart surgery, cardiac catheterization or both and have met with limited success. While there are drugs for the treatment of AF they need to be delivered quickly requiring IV or other rapid form of administration which the patient is not capable of in a healthy condition let alone when stricken with an episode of AF. Thus, there is a need for improved methods for the treatment of atrial fibrillation.

The current trend in many medical treatments requires the delivery of a drug to a specific target site so as to avoid the toxicity to other tissue and more precisely, as well controlling the timing and amount of drug delivered to that site. In many cases, this can require an implantable drug pump. However, due to their size and power requirements the current available pumps do not lend themselves to all medical applications, particularly for delivery of medication to the brain and other tissues, where very precisely controlled doses of drug can be required. Also current devices can require frequent replenishment of the drug due to limited reservoir size and/or limited shelf life of the drug. Thus, there is a need for improved implantable drug delivery devices and associated methods for in vivo drug delivery.

SUMMARY OF THE INVENTION

Embodiments of the invention provide apparatus, systems methods and formulations for delivering medication in solid form to various locations in the body. A preferred embodiment is directed to an apparatus for delivery of medication to a delivery site within the body of a patient. The apparatus comprises a drug storage device configured to be implanted within the patient's body, that is configured to store a plurality of solid form medication elements, each medication element comprising a drug. In many preferred embodiments the apparatus further comprises means for dissolving or suspending the at least one solid form medication element with a bodily fluid or mixture of bodily fluids to form a liquid drug solution or suspension. The terms dissolve and suspend are hereinafter used interchangeably, for the purposes of this application the term solution also encompasses a suspension. Likewise, the terms solution and suspension are used interchangeably. In many preferred embodiments the apparatus also further comprises a means for delivering the drug solution to the delivery site. In many preferred embodiments the delivery site is solid tissue. The solid tissue may comprise a surface of a heart.

In some embodiments, the means for dissolving or suspending the at least one solid form medication element with a body fluid comprises a flexible delivery member having a proximal and distal end, the proximal end coupled to the drug storage device. The delivery member also includes a lumen for the advancement of the medication element through the delivery member. Such means for dissolving or suspending the medication element may further comprise an advancement member configured to advance the medication element through the delivery member lumen and a capture member coupled to the distal end of the delivery member. The capture chamber includes a housing having an interior volume for receiving the medication element, the housing may also include at least on porous section allowing tissue fluids to enter and exit the chamber. The chamber is configured to retain the medication element received from the delivery member and dissolve or suspend the medication element in the tissue fluids within the interior volume to form a drug solution. Many preferred embodiments further comprise a means for delivering the drug solution or suspension to the delivery site. The means for delivering the drug solution or suspension to the delivery site comprise at least one porous section of the capture chamber configured to deliver the drug solution to the delivery site. The porous section allows the drug solution to pass from the capture chamber into the delivery site. To facilitate this delivery, in many preferred embodiments the at least one porous section includes a tissue contacting porous section configured to contact tissue so as to deliver the drug solution to the delivery site. In some embodiments the at least one porous section may further comprise a non-tissue contacting porous section. The tissue contacting section may have a first porosity and the non-tissue contacting section may have a second porosity.

Many embodiments provide an implanted apparatus for delivering solid form medication including one or more drugs to the heart for treatment of conditions such as various forms of arrhythmia (e.g., atrial fibrillation) or other cardiac conduction disorder. Particular embodiments provide an implanted apparatus for delivering solid form medications such as pellets or other solid form medication element to a myocardial delivery site on the surface of the heart to treat atrial fibrillation.

In one embodiment, the invention provides an apparatus for treatment of cardiac arrhythmia or other cardiac conduction disorder comprising a drug delivery member coupled to a drug storage device. The drug storage device is configured to both store drug and advance drug through the drug delivery member to a target tissue site in the heart or other location. In many embodiments, it includes a drug advancement means such as a stylete which is advanced by electrically driven rollers or other drive means. The drug storage device can be implanted subcutaneously in the pectoral area or other region on the patient's torso. Also, it may be incorporated into a pacemaker housing or into the housing for another device used to send electrical signals to the heart. Alternatively, it may be have its own housing which may be placed in the same or a different location as the pacemaking device.

The drug delivery member will typically comprise a catheter having one or more lumens for delivery of the drug pellet to the myocardium. The catheter may comprise any number of biocompatible polymers known in the art. In many embodiments, the catheter will also include at least a first and second electrical lead for sensing electrical activity of the heart. The leads comprise any conductive metal and are desirably insulated for most of their length. They may be coiled around the perimeter of the catheter and/or placed within a lumen of the catheter separate from the drug delivery lumen. In preferred embodiments, all or a portion of the catheter may comprise a first (an inner) and second (outer) tubular member (also referred to as inner and outer catheters) concentrically arranged with the leads positioned between the two tubular members. Desirably, this configuration is used for at least the mid portion of the catheter, but it may be used for substantially the entire length the catheter. In a specific preferred embodiment, the leads are coiled around the outer perimeter of the first tubular member with the second tubular member then jacketing the leads and the inner member. The coiled leads may also be arranged to provide torsional support to the catheter so as maintain patentcy of the drug delivery lumen if the catheter is put in a bent, twisted or crimped position. In another embodiment for supporting the drug delivery lumen to maintain patentcy, the lumen can include a support coil, such as 0.005" trifilar wire wound around the inner surface of the lumen. The tubular members can comprise silicone rubber (or other biocompatible elastic material known in the art) so as to allow the catheter to bend and flex so as to have a distal section placed in various locations on the heart wall and be connected to the drug storage device.

The catheter has one end (the proximal end) coupled to the drug storage device and the other end (the distal end) coupled to a drug capture chamber described below which may be positioned adjacent a section of the myocardium. In some embodiments, the apparatus does not include the capture chamber and thus the distal end of the catheter may be positioned adjacent the myocardium. The catheter is configured to allow the solid drug pellets to be advanced from the drug storage device through the catheter lumen and then be directly ejected on or near the surface of the heart or be ejected into a capture chamber that is positioned in proximity to a wall (e.g., of the atria) of the heart (e.g., the myocardial wall) In many embodiments, the catheter is configured to place the pellet in proximity to the epicardial surface of the heart. However, placement at other locations including the endocardial surface within the left or right atrial or ventricular chambers is also contemplated. The drug pellet is configured to dissolve when so placed and deliver a therapeutically effective amount of drug for terminating and/or otherwise mitigating the episode of atrial fibrillation or other related condition. The drug pellet is transported through an inner lumen of the catheter or other like structure (e.g., a hypotube) by means of an advanceable stylete or advancement member that is advanced from the drug storage device by an electric motor or other advancement means. According to one or more embodiments, the stylete may comprise a metal wire or ribbon that is wound for example in a spool and then unwound by drive means such as electrically driven pinch rollers. The stylete will typically have a ball tip that is sized to push the drug pellet through drug delivery lumen and out the septum; however other shapes are also contemplated such as hot dog shape, or a concave shaped tip having a concavity sized to engage the diameter of the drug pellet. Also the stylette tip may be configured to sense contact with the drug pellet so as to be able to determine that the pellet is being advanced and that the pellet has been ejected. This can be accomplished by configuring the tip and/or the stylete to be capacitively coupled to the drug pellet so as to sense changes in capacitance when the tip makes and breaks contact with the drug pellet.

In many embodiments, the distal tip of the catheter is coupled to a capture chamber which is configured to hold the drug pellet while allowing blood or other floods to flow or seep into the chamber and then flow or seep out. This allows the drug to be dissolved by blood (or other fluids) which flow or seeps into the chamber and then delivered to the myocardium as the blood or other fluid flows or seeps out. The capture chamber will typically comprise a non-porous section and a porous section. In some embodiments substantially all of the capture chamber can be porous. The non-porous sections of the housing can comprise various biocompatible polymers known in the art and its blood contacting surfaces may comprise one or more non-thrombogenie materials known in the art such as silicone, polyurethane and expanded polytetraflouroethylene (ePTFE) and example of which includes TEFLON. Also one or both of the non-porous and porous sections can include a drug eluting coating configured to elute a drug to reduce thrombus formation and platelet adhesion. Such coatings can include paclitaxel and other antithrombogenie coatings known in the art.

Typically, the porous section comprises a portion (e.g., the bottom portion) of the housing positioned in contact with or close proximity to a myocardial wall. However, in some embodiments all or multiple portions (e.g., the bottom and sides) of the capture chamber can be fabricated from porous materials. The porous section can be fabricated from any number of porous biomaterials such as various polymeric fiber materials such as polyethylene teraphalate (PET) or NYLON. In preferred embodiments, the chamber can be fabricated from porous DACRON, such as a DACRON mesh, which can be either woven or knitted. The size and porosity of the porous section can be selected to allow blood (or other tissue fluid) to seep in or out of the chamber at a selected rate to in turn achieve a selected rate of disintegration of the drug pellet. In some embodiments, the porous sections of the capture chamber can be fabricated from porous materials having varying porosity. For example, for embodiments where most of the chamber is porous, the top and sides of the chamber can be fabricated from a material having a first porosity, while the portion in contact with the myocardial wall (the bottom portion) can be fabricated from a material having a second porosity, typically higher than the first porosity so as to retain blood or other fluid having the dissolved drug within the chamber while allowing it to readily wick out on the surface in contact with the myocardial wall so as to bathe the contacted myocardium with a solution (blood or other bodily fluid) containing the drug. In use, embodiments of the chamber having such a directionally varying porosity serve to improve delivery of drug to the myocardial wall both in terms of amount and rate of delivery.

The capture chamber is desirably positioned adjacent or near the myocardial wall so as to retain a drug blood solution adjacent the wall and then transport drug into the myocardium by transdermal delivery, e.g., by diffusion into myocardial wall. In many embodiments, the capture chamber is fixed to the myocardial wall by means of a helical wire (coupled to the chamber) or other fixation device that is anchored into the heart wall. Embodiments of the invention contemplate a number of configurations for the helical wire having varying pitch and number of coils. In many embodiments, the helical wire comprises an insulated tip section of the one of the electrical leads (the tip section also serves to as electrode to make electrical contact with the myocardial tissue). Other anchoring means are also contemplated.

The distal tip of the catheter extends into the capture chamber and may include an elastic self-closing septum for preventing fluid intrusion into the inner lumen. The septum includes a slit which is configured open when the drug pellet is advanced against the slit so as to allow passage of the drug pellet through the septum and then close to prevent blood or other fluid ingress into the catheter lumen.

In many embodiments, the apparatus is coupled to a controller for controlling one more aspects of the medication delivery process including actuation and control of the drive source to deliver a medication pellet into the myocardium or other location. The controller can be programmed to include a delivery regimen wherein medication is delivered at regular intervals (e.g., once or twice a day, etc.) over an extended period. It can also be configured to receive a signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of arrhythmia) or longer term changes in the patient's condition or diagnosis.

The controller can be coupled to or otherwise receive inputs from the pacemaker or a sensor. When the controller receives an input from the sensor indicative of a condition such as an episode of arrhythmia, it initiates the delivery of one or more medication pellets to the heart or other target tissue site so as to treat the medical condition. Both the initial and subsequent inputs from the sensor can be used to titrate the delivery of medication pellets over an extended period until the condition is dissipated or otherwise treated. The controller can also receive inputs from other sensors configured to measure the tissue concentration of the delivered drug. These inputs can also be used to titrate the delivery of the medication to achieve a selected concentration of drug (e.g., in plasma, tissue, etc). The drug sensors can be positioned on distal portions of the drug delivery device such as on the catheter or the outside of the porous chamber, or the as well as other sites in the body (e.g., a vein or artery) in order to develop a pharmacokinetic model of the distribution of the drug at multiple sites in the body. The apparatus can also include a sensor coupled to the controller which indicates when the medication pellets have been used up and/or exactly how many are left. The controller in turn can signal this data to an external communication device such as a cell phone, portable monitor or remote monitor (e.g., at the physician's office). In this way, the patient and/or medical care provider can take appropriate action before the apparatus runs out of medication.

The pellets or other solid form of medication are delivered to a delivery site such as the endocardial or epicardial surface of the heart where they are configured to be broken down, disintegrate and absorbed by body tissue fluids so as to produce a desired concentration of the drug at a target tissue site such as the myocardial wall. In some applications, the delivery site can be the same as the target site, for example the heart. In other applications, the target site can be different from the delivery site, for example, the delivery site can be intramuscular tissue in the chest and the target site can be the heart or the liver. The delivery site can be adjacent the target site, for example adipose to deliver to underlying muscle tissue, or it can be placed at a non-oppositional site, for example, intramuscular delivery to reach the site of the heart. In each case, the medication pellet can include a selected dose of drug and be configured to disintegrate and be dissolved by body tissue fluids so as to yield a therapeutically effective concentration of the drug at the target tissue site such as the endocardial or epicardial surface of the heart. In many applications, this involves the pellet being dissolved by body tissue fluids at the delivery site (e.g., interstitial fluids bathing the epicardium or the blood bathing the endocardium) where the drug then diffuses into the myocardial wall. Accordingly, in these and other applications, the dose of the drug in the pellet can be titrated to achieve a selected concentration of the drug (or concentration range) for a selected period of time during and after dissolution of the pellet.

In many embodiments, the pellet (including the drug dose) is configured to disintegrate and be dissolved by blood or tissue fluids which seep or otherwise enter into the porous chamber. In particular embodiments for treating various cardiac rhythm disorders such as arrhythmia, the pellet is configured to rapidly disintegrate and be dissolved in blood or other fluid within the porous chamber. This can be achieved through the use of one or more super disintegrants as well as disintegrating enhancing features (e.g., pores, cracks or other intrusions) in or one the pellet. The particular selection of disintegrants can be matched to the fluid and flow conditions within the capture chamber. Faster disintegrants can be used in chambers where the flow rate into the chamber is slower and/or the viscosity of the fluid is higher (e.g., blood vs. interstitial fluids). It can also be achieved by treating the pellet prior or after delivery into the capture chamber with mechanical, electromagnetic, acoustical or other energy to weaken the pellet structure, create cracks and other structural defects for the ingress of fluids or initiate the breakup of the pellet into smaller pieces.

In various applications, embodiments of the invention can be used to deliver solid form drugs to provide treatment for a number of medical conditions including coronary arrhythmia's (both atrial and ventricular), coronary ischemia (e.g., from a narrowed or blocked artery including that resulting in a heart attack), cerebral ischemia, stroke, anemia or other like condition. The apparatus can be implanted at or near the target tissue site (e.g., the heart) or at remote delivery site (e.g., intramuscularly in the chest or thigh In an exemplary embodiment of a method for using the invention, the apparatus can be implanted at or near a selected delivery site such as the heart. For embodiments where the device is used to deliver drug to the myocardial wall, the lead and porous chamber can be fixed to the endocardial or epicardial wall using the corkscrew fixation element or other fixation device. Implantation can be done using an open or minimally invasive procedure, for example, via percutaneous access through the vascular system. Prior to implantation, the drug reservoir can be loaded with a selected number of pellets to provide for delivery of pellets to the delivery site over an extended period of time, e.g., years. Once implanted, the pellets can be stored in the apparatus for an extended period of years (e.g., 1, 2, 5 or longer) without degradation or deleterious effect to the pellets (e.g., loss of drug potentcy or therapeutic effectiveness). The apparatus can deliver solid form medication to the delivery site at regular intervals (e.g., once a day, week, month, etc) or in response to an input from a sensor. In the latter case, the input can be indicative of a particular medical condition or event such as an episode of arrhythmia. Embodiments of the controller described herein can be used to determine when to initiate delivery based on the sensor input and/or the time intervals for delivery for embodiments employing delivery at regular intervals. In either case, the controller can send a signal to the drug storage device. There it disintegrates/degrades and is dissolved in local tissue fluids to treat a local target tissue site (e.g., it dissolves in the CSF to treat the brain), or it is subsequently absorbed into the blood stream where it is carried to a remote target tissue site (e.g., the liver, heart, etc) or both. Further pellets can be delivered based on input from a sensor providing physiologic data predictive of the medical condition (e.g., blood glucose) or another sensor that is configured to sense the local and/or plasma concentration of the drug. In some embodiments, pellet delivery can be controlled by sensing the state of disintegration of previously delivered pellets. For example, another pellet can be delivered when it has been determined that the previous pellet is in a particular state of disintegration (e.g., it has been completely or substantially disintegrated). This can be achieved by sending and receiving a signal from the pellet such as an optical, ultrasound or electrical signal. For example, for the use of optical signal reflectance measurements can be used to determine the state of disintegration. A particular disintegration state can be determined when the reflectance signal falls below a particular threshold. Similar approaches can be used for use of reflected ultrasound or impedance. The pellet can even include various echogenic, or optically opaque or other agents to enhance the reflected ultrasonic, optical or other signal. The pellet may also include various optical indicia having one or more of a pattern, size or shape configured to provide an indication of the state of disintegration of the pellet.

Further details of these and other embodiments and aspects of the invention are described more fully below, with reference to the attached drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1b is a perspective view showing an embodiment of a drug delivery apparatus including a drug delivery catheter, electrical lead and capture chamber; the figure also shows connectors used for the delivery catheter and electrical lead.

FIG. 1c is a top view showing the distal portion of the catheter and the capture chamber of the embodiment of FIG. 1b.

DETAILED DESCRIPTION OF THE INVENTION

Figure 1A:
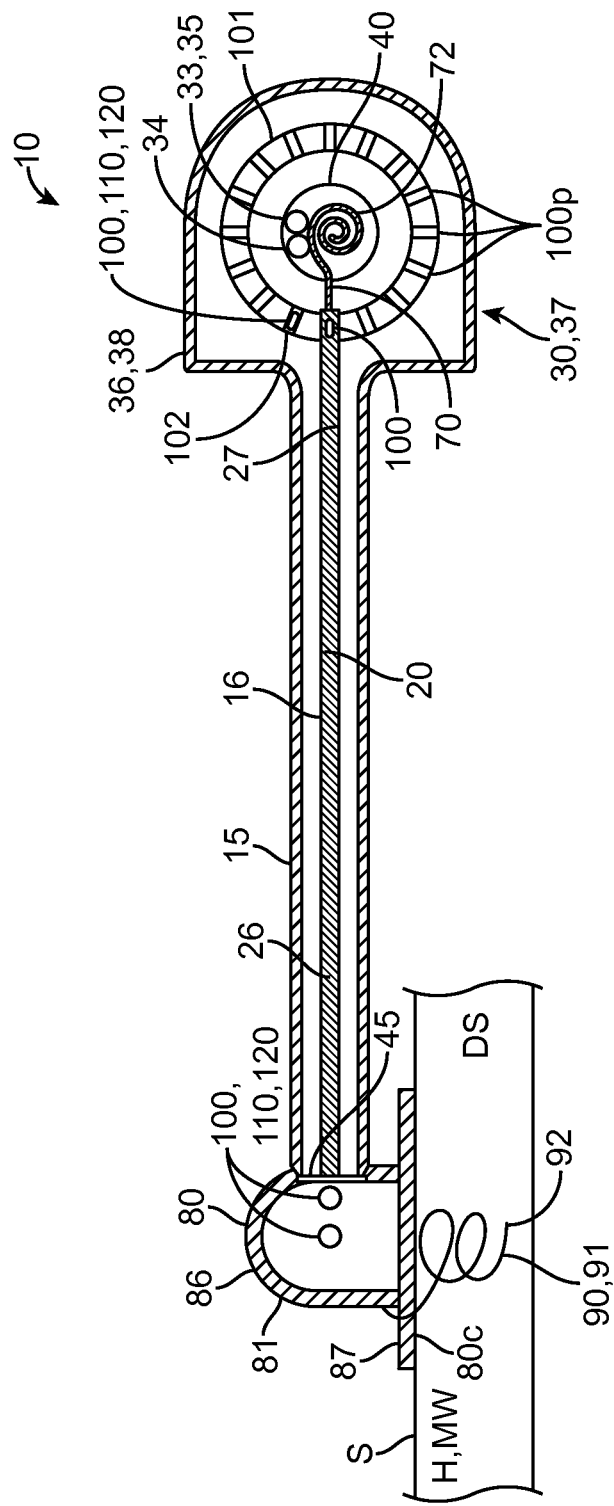
FIG. 1a is a lateral view showing an embodiment of a drug delivery apparatus.

Embodiments of the invention provide apparatus, systems, methods and formulations for delivering medications in solid form to various locations in the body. Many embodiments provide an implanted apparatus for delivering solid form medication to the heart for treatment of conditions such as various forms of arrhythmia (e.g., those resulting in atrial fibrillation) or other cardiac conduction disorder. Particular embodiments provide an implanted apparatus for delivering solid form medication to a myocardial delivery site on the surface of the heart to treat atrial fibrillation.

Referring now to FIGS. 1-8, in one or more embodiments, the invention provides an apparatus 10 for the treatment of cardiac arrhythmias comprising a drug delivery member 20 coupled to a drug storage device 30. Delivery member 20 has a distal end 20de positioned at or near a delivery site DS on or near the heart H or other location. In various embodiments described herein, delivery member 20 can be coupled at its distal end 20ed to a capture chamber 80 positioned on the surface S of a delivery site DS such as myocardial wall MW of a patient's heart H so as to deliver drug to the heart for the treatment of cardiac arrhythmias.

Delivery member 20 may be contained in an outer sheath 15 which also contains one or more electrical leads 50 (described herein) for sending and receiving electrical signals to and from the heart. Sheath 15 may be fabricated from various biocompatible resilient polymers known in the art (e.g., polyurethane, silicone, PEBAX, HDPE, etc.) and has at least one lumen 16 for delivery member 20 and lead 50. The drug storage device 30 is configured to both store a solid form medication 100 and advance the drug through the drug delivery member 20 to a delivery site DS on/in the heart or other location.

Solid form medication 100 also described herein as formulation 100, medication 100 or medication element 100, will typically be formulated into pellets 100, though other solid formulations are also contemplated. For ease of discussion, solid form medication 100 will now be referred to as medication pellets 100 and/or pellets 100, but it will be appreciated that other forms of solid medication 100 are equally applicable. Medication 100 typically comprises one or more drugs or other therapeutic agents 110 for the treatment of one or more conditions. Medication 100 may also include one or more pharmaceutical excipients 120 including for example, one or more of disintegrants, super-disintegrants, binders, anti-oxidants and other excipients known in the art. In case of various cardiac applications, including applications where the medication pellet 100 is configured to dissolve within capture chamber 80, the dis-integrant can be selected or otherwise adjusted to allow for rapid disintegration in bodily fluids such as one more of blood and/or interstitial fluid which bathes the epicardium and/or pericardium.

In various embodiments pellets 100 can comprise various drugs and other therapeutics agents 110 for the treatment of cardiac arrhythmias and related cardiac conduction disorders. In particular embodiments, such drugs and other therapeutic agents can comprise cholinergic compounds such as atropine, scopalomine or methylscopalomine; sodium channel blockers such as, quinidine, procainamide, disopyramide or lydocaine; and cardiac glycoside such as digoxin or digitoxin. Further, as is described elsewhere herein, since these drugs are being delivered near to and/or directly to the surface of the heart, the dosage of drug to treat the arrhythmia can be titrated to produce the desired therapeutic effect while reducing or preventing adverse effects or reactions which may result from larger doses when the drug is delivered orally and/or parenterally (e.g., via IV). For example, in the case of sodium channel blockers for the treatment of arrhythmia (e.g., quinidine, procainamide and disopryamide) the dosage of drug can be titrated to prevent or reduce the severity or incidence of adverse reactions such as one or more of tachycardia, dry mouth, urinary retention or blurred vision. For example, in the case cardiac glycosides for the treatment of arrhythmia (e.g., Digoxin or Digitoxin) the dosage of drug can be titrated to prevent or reduce the severity or incidence of adverse reactions such as atrial tachycardias, atrioventricular block and various forms of digitalis toxicity. Such titrations can be done using dose response curve methods known in the art.

In particular embodiments, where atropine is used, the dose of this drug (and/or its analogues or derivitives) delivered by various embodiments of the can be in a range from about 1 to 500 micrograms, or 2 to 250 micrograms, or 5 to 100 micrograms, or 1 to 10 micrograms, or 1 to 20 microgram per dose. In embodiments where scopolamine is used, the dose of this drug (and/or its analogues or derivitives) delivered by one or more embodiments of the invention can be in a range from about 0.1 to 50 micrograms, or 0.2 to 25 micrograms, or 0.50 to 10 micrograms, or 0.50 to 5 micrograms per dose. In embodiments where lidocaine is used the dose of this drug (and/or its analogues or derivitives) delivered by one or more embodiments of the invention can be in a range from about 10 to 1000 micrograms, or 20 to 500 micrograms, or 50 to 250 micrograms, or 1 to 10 micrograms, or 1 to 5 micrograms per dose. Other dosage ranges are also contemplated. The dosage may be titrated based on one or more factors such as the patient's age, particular cardiac arrhythmia, its severity and other medications that the patient is receiving. In one or more embodiments of the invention, the aforementioned dosages are stored in apparatus 10 and delivered in solid form to capture chamber 80 where they are dissolved in tissue fluids (either blood or interstitial fluids) and delivered to the myocardial wall (either the endocardial or pericardial wall) of the left or right atria.

In various embodiments, pellets 100 can comprise a single or a plurality of drugs 110. In particular embodiments, pellets 100 can include a combination of drugs for treatment of a single or multiple conditions, for example, a cocktail of drugs for the treatment of various cardiac conditions such as arrhythmia, angina, myocardial infarction, stroke; a cocktail of antiviral drugs such as protease inhibitors for treatment of HIV AIDS and also antibiotics for the treatment of adjunct bacterial infections.

The drug storage device 30 can be implanted subcutaneously in the pectoral area or other region on the patient's torso. In one or more embodiments, the drug storage device 30 may be incorporated into a housing 36 of a pacemaker or other cardiac device 37 used to send electrical signals to the heart. Alternatively, it may be have its own housing 38 which may be placed in the same or a different location as pacemaker or other cardiac device 37.

Drug pellet 100 or other solid form drug 100 can be stored in drug storage device 30 in a variety of configurations. In preferred embodiments, pellet 100 are contained in/on a belt 101 containing a plurality 100p of drug pellets 100 which may be stored in individual packing containers 102 attached to belt 100. Pellets 100 can be removed from belt 101 and advanced out of storage device 30 through use of a drug advancement means 40. In many embodiments, advancement means 40 corresponds to a stylete or other advancement member 70 that is configured to advance pellet 100 from storage device 30 into catheter 20 and capture chamber 80. Stylett 70 can be advanced by a drive means 33 which may correspond to rollers 34 driven by an electric motor 35. In a particular embodiment, stylete 70 is advanced by two opposing rollers, 34 driven by an electric motor.

The drug delivery member 20 will typically comprise a catheter 20 or other like flexible member having one or more lumens 21 which have an internal diameter 21d sized for delivery of a drug such as drug pellet 100 to the myocardium or other tissue site. Catheter 20 may have other lumens 22 which may be configured for other purposes besides drug delivery such as placement of one or more electrical leads 50. The catheter 20 may comprise any number of biocompatible resilient polymers known in the art (e.g., silicone, PeBax, polyurethane, polyethylene (e.g., HDPE, LDPE), etc.) and may be formed using various extrusion methods also known in the art.

In many embodiments, catheter 20 has one end 20*e* (the proximal end 20*ep*) coupled to the drug storage device 30 and the other end 20*e'* (the distal end 20*ed* also referred to as distal tip 20*ed*) coupled to a drug capture chamber 80 described below which is positioned adjacent a section of the myocardium. Proximal end 20*ep* of catheter 20 can include or be coupled to a connector 20*c* known in the medical device/ catheter arts such as a luer-lock, snap fit or swaged connector for coupling to drug storage device 30. The connector 20*c* has a sufficient inner diameter to accommodate drug pellet 100 (as does catheter lumen 21) and also desirably provides a watertight seal for preventing tissue fluids from getting into drug storage device 30.

In some embodiments, apparatus 10 does not include a capture chamber 80 and in these cases, catheter distal end 20*ed* may be configured to be positioned in or near the heart (and may include a fixation device described herein) so as to release drug pellet 100 directly to the myocardial wall MW. In such embodiments, catheter distal end 20*ed* is desirably configured to have an atraumatic tip 20*at* to minimize or prevent injury or irritation to the myocardial wall or other tissue. This can be achieved by configuring the tip to have a rounded and/or tapered shape (as shown the embodiment of FIG. 6*b*) as well as through the use of soft low durometer polymer materials known in the art such as hydrogels and silicone. In particular embodiments, an atraumatic tip 20*at* can be fabricated from silicone materials having a durometer of between 1-20 Shore A, more preferably between 1-10 Shore A and still more preferably between 1-5 Shore A.

Catheter 20 is configured to allow solid drug pellets 100 (or other shape/form of solid form medication 100) to be advanced from the drug storage device 30 through the catheter lumen 21 and then be directly ejected on or near the surface of the heart or be ejected into a capture chamber that is positioned in proximity to a myocardial wall (e.g., of the atria). In many embodiments, catheter 20 is configured to place the pellet in proximity to the epicardial surface of the heart. However, placement at other locations including the endocardial surface within the left or right atrial or ventricular chambers is also contemplated. The drug pellet 100 is configured to dissolve (in blood and/or other tissue fluids) when so placed and deliver a therapeutically effective amount of drug for terminating and/or otherwise mitigating the episode of atrial fibrillation or other related condition.

Figure 2:
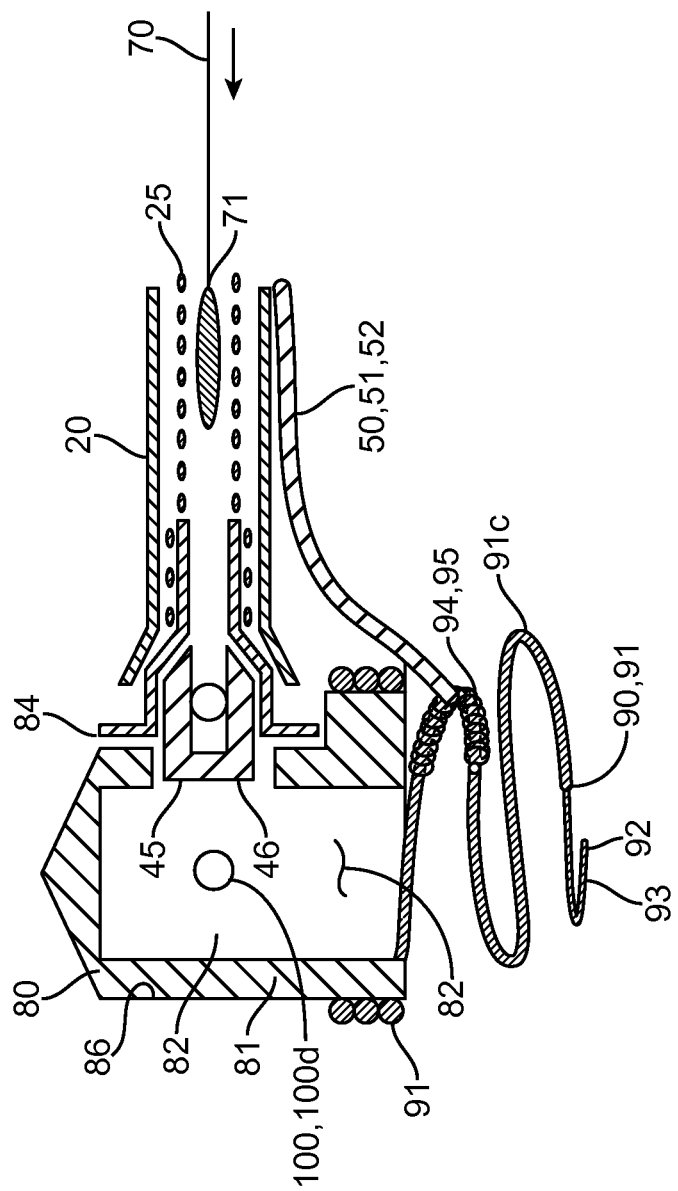
FIG. 2 is a cross sectional view of the distal portion of the catheter, the capture chamber and a cork screw fixation device, it also illustrates ejection of a drug pellet from the catheter into the capture chamber.
Figure 6A:
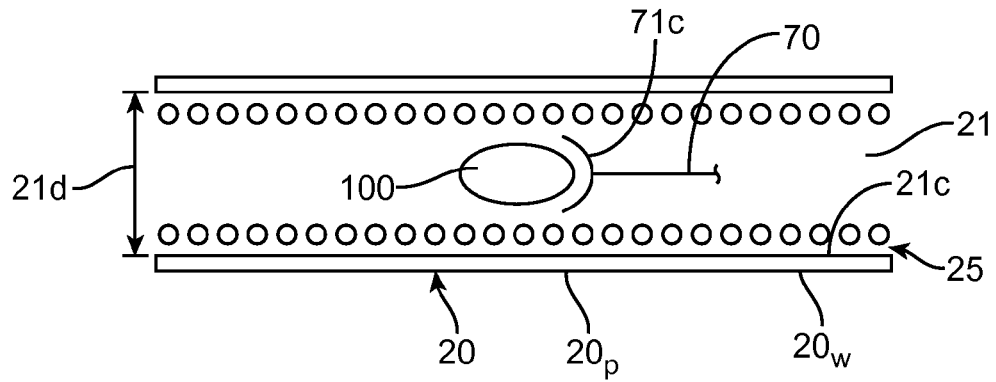
FIG. 6a is a cross sectional side view showing the drug delivery lumen of an embodiment of the drug delivery catheter.
Figure 6B:
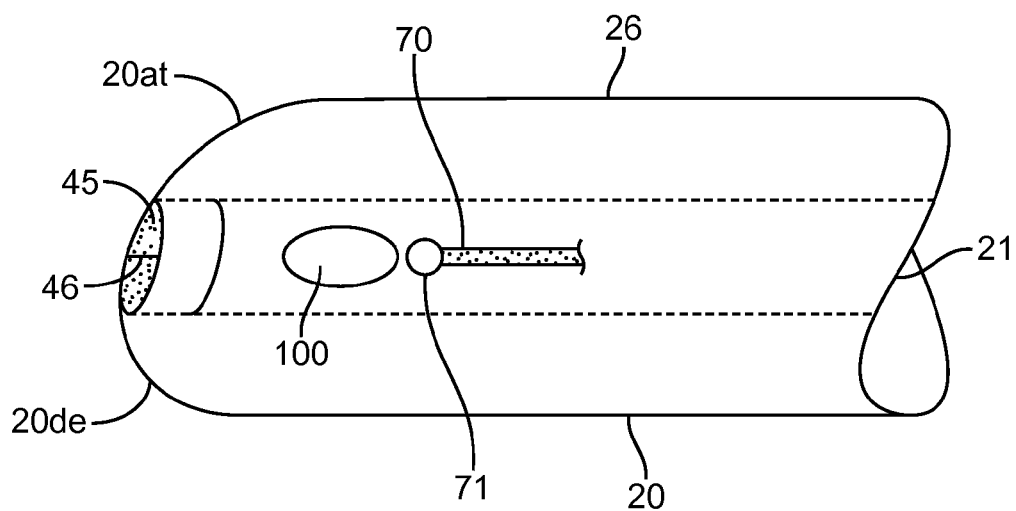
FIG. 6b is a perspective side view showing an embodiment of the delivery catheter having an atruamatic tip for delivery of a drug pellet to a delivery site without use of a capture chamber.
Figure 7A:
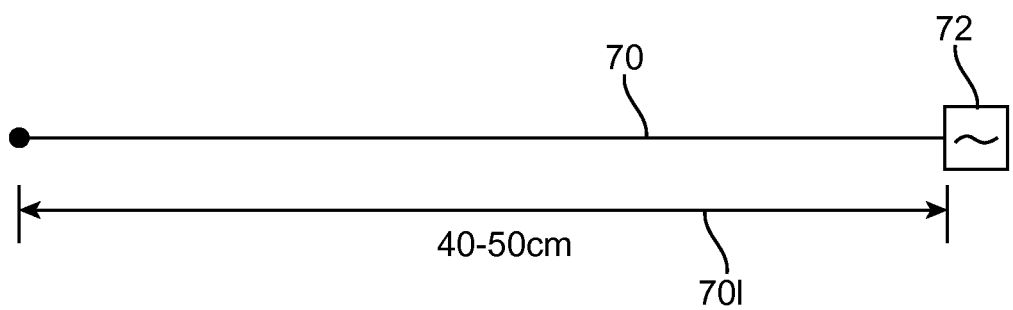
FIG. 7a shows an embodiment of the drive stylete having a ball tip.
Figure 7B:
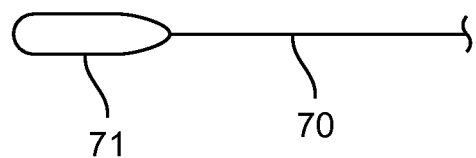
FIG. 7b shows an alternative embodiment of the tip of the drive stylete.
Figure 8:
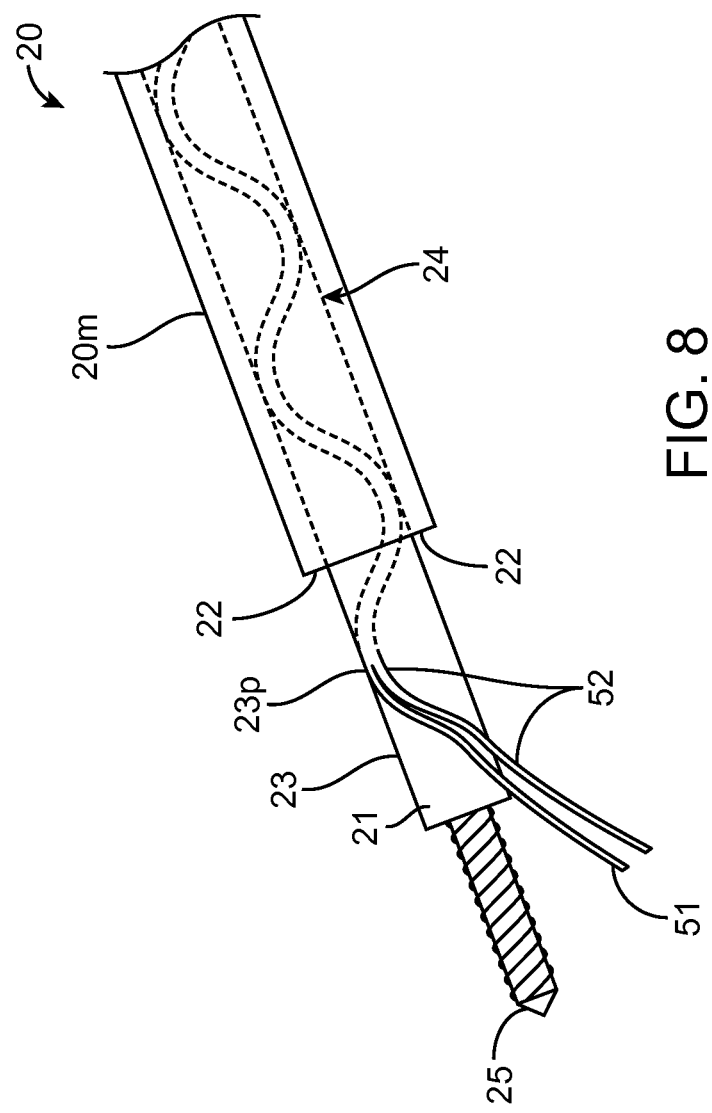
FIG. 8 is a perspective view illustrating an embodiment of drug delivery member including an inner and outer member.

In preferred embodiments, all or a portion of catheter 20 may comprise a first (an inner) and second (outer) tubular member 23 and 24 (also referred to as inner and outer catheters 23 and 24) concentrically arranged with one or more electrical leads 50 such as electrical leads 51 and 52 (described below) positioned between the two tubular members. Desirably, this configuration is used for at least the mid portion 20*m* of the catheter, but it may be used for substantially the entire length of catheter 20. In a specific preferred embodiment, leads 51 and 52 are coiled around the outer perimeter 23*p* of the inner member 23 with the outer member 24 then jacketing the leads and the inner member 23. Coiled leads 51 and 52 may also be arranged to provide torsional support to the catheter 20 so as maintain patentcy of the drug delivery lumen 21 if the catheter is put into a bent, twisted or other contorted position. In other embodiments for supporting the drug delivery lumen to maintain patentcy, lumen 21 can include a support coil 25, such as a 0.005" trifilar wire wound around the inner surface 21*i* of the lumen 21 as is shown in the embodiments of FIGS. 2 and 6. In such embodiments support coil 25 may have a lubricous coating, for example, a TEFLON coating, to facilitate passage of drug pellet 100 through the lumen 21. In an alternative embodiment support coil 25 can be positioned around the exterior of lumen 21 and thus within catheter wall 20*w*. Such embodiments can be produced using co-extrusion methods known in the catheter and polymer processing arts.

Inner and outer members 23 and 24 can comprise an elastomeric material such as silicone (or other elastic material known in the art) so as to allow the catheter 20 to bend and flex so as to be positioned in different locations in the body. In particular embodiments, catheter is 20 is sufficiently flexible so as to be able to position the distal portion 26 of the catheter in various locations on or near the heart wall (e.g., on the right or left atria) while allowing the proximal portion 27 of the catheter to be connected to drug storage device 30.

As described above in one or more embodiments, apparatus 10 includes one or more electrical leads 50 for performing one or more of the following functions: i) sensing electrical activity of the heart; ii) pacing the heart; iii) sending an electrical signal to the heart to depolarize a selected area of the myocardium (e.g., an area containing a foci of aberrant electrical activity); and iv) sending an electrical signal to the heart to defibrillate one or more chambers of the heart. Leads 50 can placed within sheath 15, catheter 20 or both. They may comprise various insulated conductive wires (also described as cables) known in the art which are configured for use in pacemakers and other cardiac stimulation devices known in the art such as ICD (implantable cardiac defibrillators). At their proximal end 50*p*, they will typically include an electrical connector 50*c*, such as an IS-1 connector for connection for example to a cardiac stimulation device as is shown in the embodiment of FIG. 1*b*. Lead 50 can also be configured to contain multiple leads 50. Accordingly, in one or more embodiments, lead 50 may also be of a coaxial design as is know in the art so to include a first and second lead 51 and 52 as is described below.

In many embodiments, apparatus 10 will also include at least a first and second electrical lead 51 and 52 for sensing electrical activity of the heart. The leads 51 and 52 may comprise any conductive metal and are desirably insulated for most of their length. They may be coiled around the perimeter 20*p* of catheter 20 and/or placed within a lumen 22 of the catheter separate from the drug delivery lumen 21. They may also configured as a first and second lead 50 and 51 placed within a coaxial cable 50.

Embodiments of the invention contemplate a variety of means for advancing drug pellet 100 through the lumen 21 or other lumen of drug delivery catheter 20. Such means may include, for example, mechanical, pneumatic, hydraulic or magnetic means. In preferred embodiments, drug pellet 100 is transported through drug delivery lumen 21 of catheter 20 or other like structure (e.g., a hypotube) by means of an advanceable member 70 such as a stylete 70 that is advanced from the drug storage device 30 by an electric motor or other advancement means. Stylete 70 can have a length 70*l* in the range of about 40-50 cm with longer and shorter lengths contemplated. According to one or more embodiments, stylete 70 may comprise a metal wire or ribbon that is wound, for example, in a spool 72 and then unwound by drive means 33 such as electrically driven pinch rollers 34. In a preferred embodiment the advanceable member has a wound state when not advanced and an unwound state when advanced. The metal wire or ribbon may comprise various flexible metals known in the art including super elastic metals such as NITNOL so as to readily unwind when spooled and then rewind. It may also have a preformed shape and/or be spring loaded. Other advanceable members 70 known in the catheter/guide wires arts are also contemplated.

Stylete 70 will typically have a ball tip 71 that is sized to push drug pellet 100 through drug delivery lumen and out the septum; however other shapes for tip 71 are also contemplated such as hot dog shape, or a concave shaped tip 71c having a concavity sized to engage the diameter of the drug pellet. In one or more embodiments, stylete tip 71 may be configured to sense contact with the drug pellet 100 (or other form of solid drug 100) so as to able be to determine that the pellet is being advanced and/or that the pellet has been ejected. This can be accomplished by configuring the tip and/or the stylete to be capacitively coupled to the drug pellet so as to sense changes in capacitance when tip 71 makes and breaks contact with the drug pellet.

In many embodiments, the distal tip 20ed of catheter 20 is coupled to a capture chamber 80 which is configured to hold the drug pellet 100 while allowing blood or other floods to flow or seep into the chamber and then flow or seep out. This allows the drug pellet to be dissolved by blood (or other fluids) which flow or seeps into the chamber and then delivered to the myocardium as the blood or other fluid flows or seeps out. Capture chamber 80 includes a housing 81 having an interior volume 82 in which drug pellet 100 is contained while it dissolves. The housing 80 will typically include an opening 83 for insertion of catheter 20 so as to form a joint 84 with the catheter as is shown in the embodiment of FIG. 2. The housing will also typically include a second opening 85 for placement of porous section 87 discussed below.

Joint 84 can comprise any number of those known in the art such as a weld, ultrasonic weld, adhesive joint, crimp, snap fit and the like. In particular embodiments joint 84 may comprise a pivotal type joint so as to allow the capture chamber 80 to move freely with beating of the heart while imparting reduced force and motion to catheter 20. In use, such embodiments improve the reliability and mechanical life of joint 84, chamber 80 and catheter 20 by reducing the stress imparted on one or more of these components. Such embodiments also reduce the likelihood of hemolysis caused by movement of catheter 20 by minimizing the motion of catheter within the chambers of the beating heart.

Capture chamber 80 and housing 81 will typically comprise at a non-porous section 86 and a porous section 87 both of which may comprise multiple sections 86 and 87. In some embodiments, substantially all of the capture chamber 80/housing 81 can be porous. The non-porous section(s) 86 of the housing 81 can comprise various biocompatible polymers known in the art. The blood contacting surfaces of the housing 81 (including one or both of the porous and non-porous sections) may comprise one or more non-thrombogenie materials known in the art such as silicone, polyurethane and expanded polytetraflouroethylene (ePTFE, and example of which includes TEFLON). Also, one or both of the non-porous and porous sections 86 and 87 can include a drug eluting coating 80d configured to elute a drug to reduce thrombus formation and platelet adhesion. Such coatings can include paclitaxel and other anti-thrombogenie coatings known in the art. The coating can also be selected so as not interfere with the bioactivity of medication 100 and/or to produce a synergetic effect Typically, the porous section 87 comprises a portion (e.g., the bottom portion or side) of the housing 81 that is configured to be positioned in contact with or close proximity to the myocardial wall or other portion of the heart. However, in some embodiments, all or multiple portions (e.g., sides) of the capture chamber 80/housing 81 can be fabricated from porous materials. The porous section 87 can be fabricated from any number of porous biomaterials such as various polymeric fiber materials such as polyethylene teraphalate or NYLON. In preferred embodiments, the chamber housing can be fabricated from porous DACRON, such as a DACRON mesh, which can be either woven or knitted. The size and porosity of porous section 87 can be selected to allow blood (or other tissue fluid) to seep in or out of the chamber at a selected rate to in turn achieve a selected rate of disintegration of the drug pellet. In some embodiments, porous sections 87 can be fabricated from porous materials having varying porosity. For example, for embodiments where most of chamber 80 is porous, the top 80t and sides 80s of the chamber 80 can be fabricated from a first material having a first porosity, while the portion in contact with the myocardial wall 80c (e.g., also referred to as tissue contacting portion or surface 80c) can be fabricated from a second material having a second porosity, which is typically higher than the first porosity so as to retain blood or other fluid having the dissolved drug within the chamber 80 while allowing it to readily wick out portion 80c in contact with the myocardial wall so as to bathe the contacted myocardium with a solution (blood or other bodily fluid) containing the drug, herein referred to as a drug solution. In use, embodiments of chamber 80 having such a directionally varying porosity serve to improve delivery of drug to the myocardial wall both in terms of amount and rate of delivery. For purposes of reference, tissue contacting portion 80c may also be referred to as a bottom portion 80b of chamber 80.

In many embodiments, the capture chamber 80 is positioned adjacent or near the myocardial wall so as to retain a drug-blood solution adjacent the wall and then transport drug into the myocardium by transdermal delivery, e.g., by diffusion into myocardial wall. In many embodiments, capture chamber 80 is fixed to the myocardial wall by means of a helical wire 91 (coupled to the chamber) or other fixation device 90 (also referred to as anchoring means 90) that is anchored into the heart wall. Embodiments of the invention contemplate a number of configurations for helical wire 91 having varying pitch and number of coils so as to achieve a desired level of anchoring force (up 5 lbs of force or more) within myocardial wall to retain the capture chamber against the myocardial wall even during vigorous beating of the heart. Other anchoring means are also contemplated.

In addition to functioning as fixation device, according to one or more embodiments, helical wire 91 can also be configured as an electrode 92 to sense electrical activity of the heart and to conduct electrical signals to the heart for purposes of depolarizing sections of the generating aberrant electrical activity and/or to defibrillate the atria or ventricles of the heart. To achieve this purpose, i) wire 91 is fabricated from a conductive metal core 90c having insulation 91i, ii) a distal portion 93 of wire 91 is un-insulated, and iii) wire 91 is electrically coupled to a lead 51 or 52, for example, by crimp tube or other crimp joint 53 as is shown the embodiment of FIG. 3b. In order to have a two electrodes for sending and/or receiving electrical signals to and from the heart, in many embodiments, wire fixation device 91 can include another conductive wire 94 coiled over wire 91 as is shown in the embodiments of FIGS. 1B, 2-3, 5D and 5F. Wire 94 is configured function as a second electrode 95 and can be electrically coupled to lead 51 or 52, for example, by a crimp tube or other crimp joint 53 as shown n the embodiment of FIGS. 3A and 5E. In one or more embodiments, electrodes 91 and 94 may be configured as bipolar electrodes 96 for sending and/or receiving signal to and from the heart.

Figure 3A:
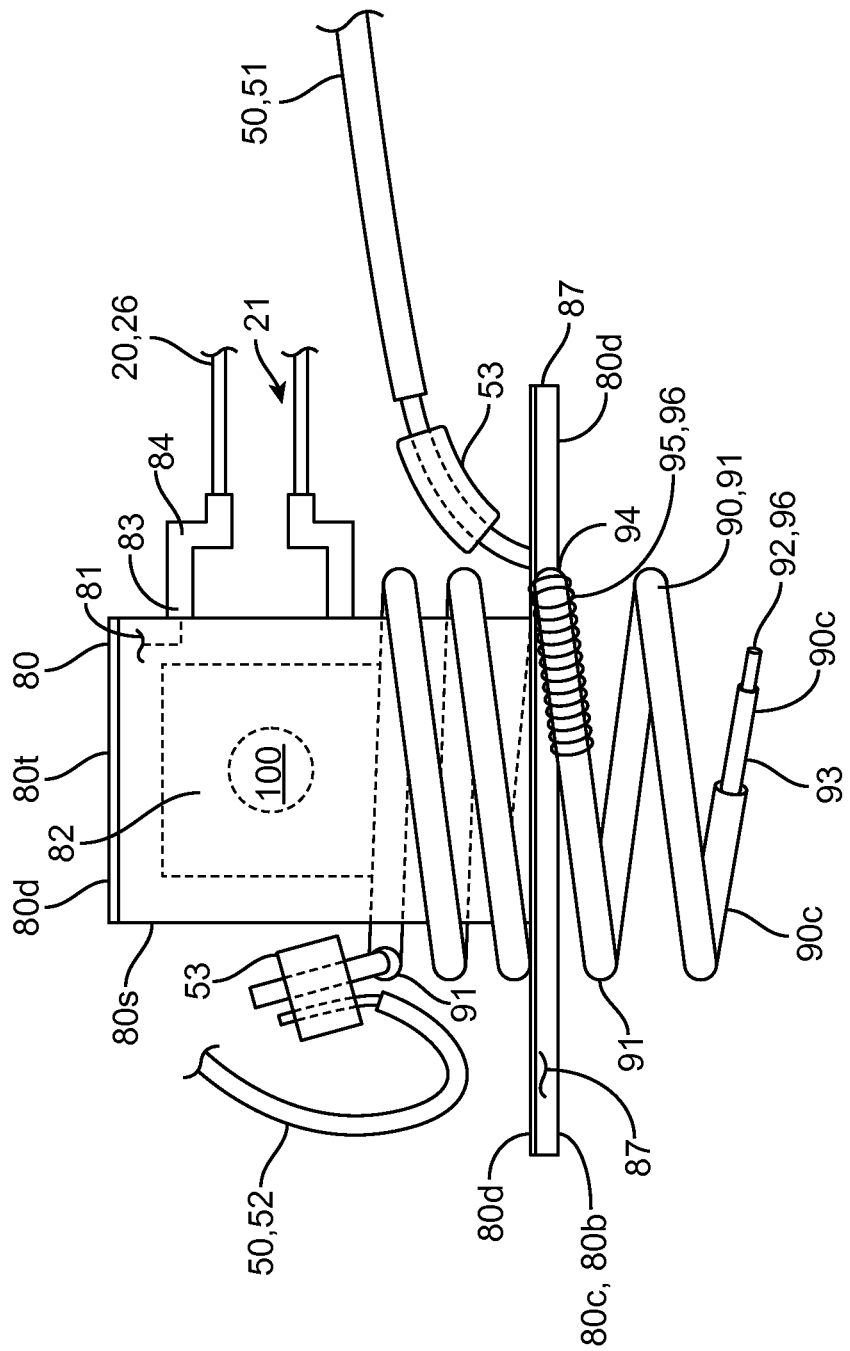
FIG. 3A is a perspective view illustrating an embodiment of the capture chamber having a cork screw fixation device and electrode and connection of the corkscrew to electrical leads of the drug delivery apparatus.
Figure 3B:
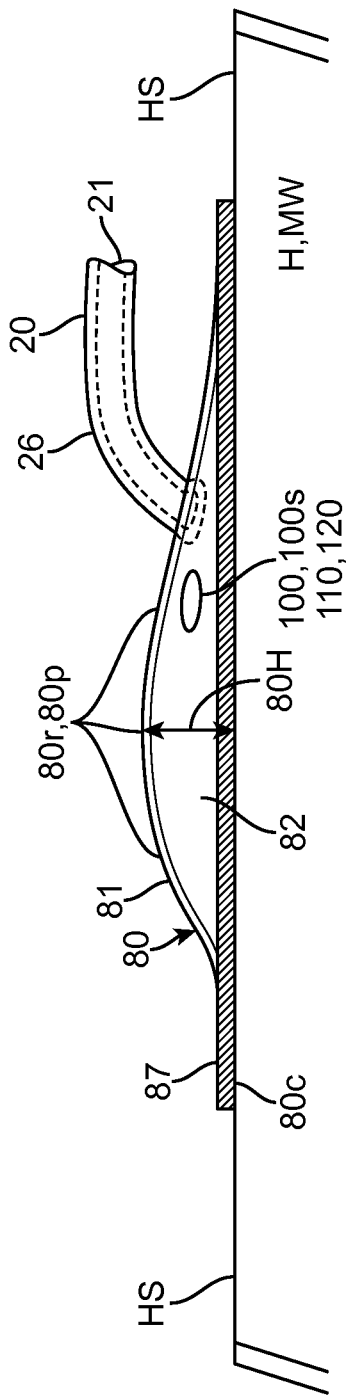
FIG. 3B is a lateral view illustrating an embodiment of the capture chamber having a curved contour for not interfering with heart wall motion and/or blood flow in the heart.
Figure 4:
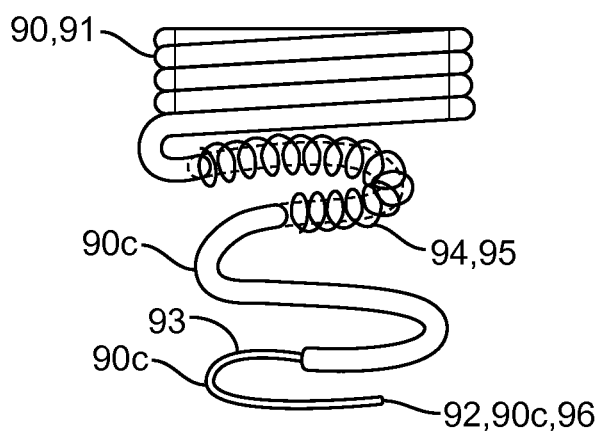
FIG. 4 illustrates an embodiment of the corkscrew fixation device and electrode.
Figure 5A:
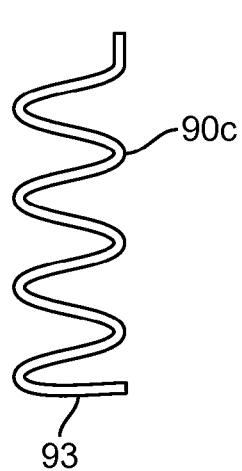
FIGS. 5A-5F illustrate components of an embodiment of the corkscrew fixation device and electrode.
Figure 5B:
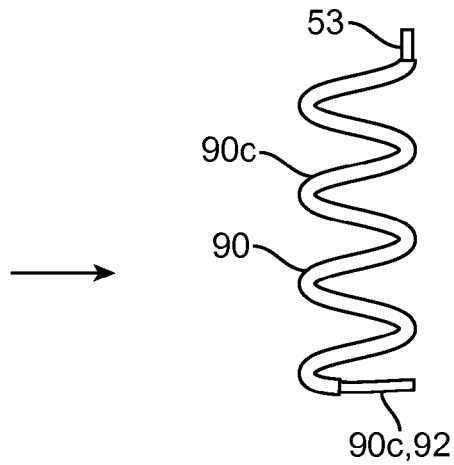
Figure 5C:
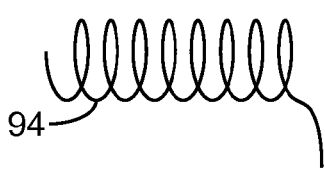
Figure 5D:
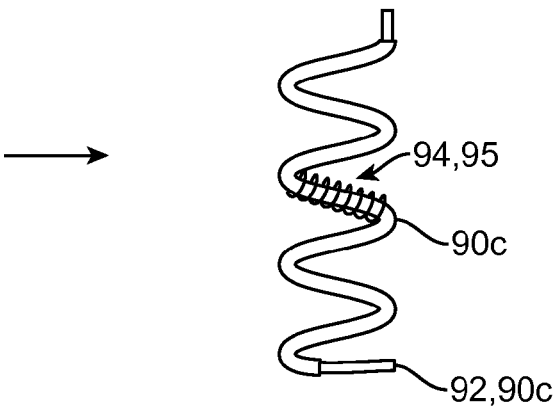
Figure 5E:
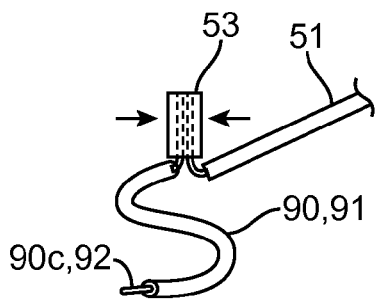
Figure 5F:
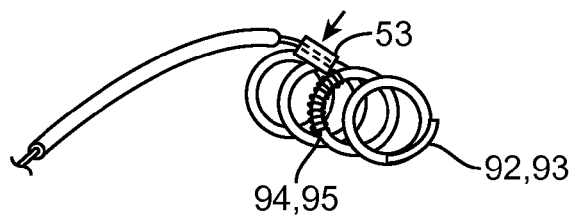

In many embodiments, the tissue contacting surface 80c of chamber 80 is sufficiently flexible to bend and flexible with beating of the heart so as to not impede heart wall motion whether it be the atrial or ventricular wall and whether surface 80c is positioned on the epicardial or endocardial surface of the heart. This flexibility can be achieved through the use of various flexible porous polymer materials for surface 80c, for example a flexible DACRON mesh. Likewise, chamber 80 can be configured not to impede heart wall motion as well. This can be achieved by the selection of the flexibility, mass and contour 80r of chamber 80. For example, various flexible polymer materials can be used for housing 81 such as silicone, polyurethane, or other elastomeric polymer known in the art. Also, the contour 80r of chamber 80 is desirably configured to minimize any impediment to blood flow in the heart whether it be in the atria or ventricles (left or right in either case) and/or to not cause any appreciable turbulence in blood flow within the heart. This can be achieved be configuring chamber 80 to have a smooth/stream lined curved contour 80r and low profile 80p such that housing 81 does not rise appreciably above the surface of the heart HS, e.g., by an amount 80 H no more than about 1 cm, more preferably, no more than about 5 mm, still more preferably no more than about 2.5 mm with even smaller amounts contemplated. One example of such a curved contour is shown in the embodiment of FIG. 3b. In such embodiments, pellet 100 can be have an elongated thinner shape 100s so as to be able to be placed within the interior 82 of a chamber 80 having such a thinner shape.

As discussed above, the distal tip 20ed of catheter 20 extends into the capture chamber 80 for ejecting pellet 100 into the chamber. In many embodiments, distal tip 20ed includes an elastic self-closing septum 45 for preventing fluid intrusion into drug delivery lumen 21 or other lumen 22 of catheter 20. Septum 45 may be resealable, Septum 45 includes a slit 46 which is configured open when drug pellet 100 is advanced against the slit so as to allow passage of the drug pellet through the septum and then close to prevent blood or other fluid ingress into the catheter lumen.

In many embodiments, the apparatus 10 is coupled to a controller (not shown) for controlling one more aspects of the medication delivery process including actuation and control of the drive source to deliver a medication pellet into the myocardium or other location. The controller can be programmed to include a delivery regimen wherein medication is delivered at regular intervals (e.g., once or twice a day, etc.) over an extended period. It can also be configured to receive a signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of arrhythmia) or longer term changes in the patient's condition or diagnosis.

The controller can be coupled to or otherwise receive inputs from the pacemaker or a sensor. When the controller receives an input from the sensor indicative of a condition such as an episode of arrhythmia, it initiates the delivery of one or more medication pellets to the heart or other target tissue site so as to treat the medical condition. Both the initial and subsequent inputs from the sensor can be used to titrate the delivery of medication pellets over an extended period until the condition is dissipated or otherwise treated. The controller can also receive inputs from other sensors configured to measure the tissue concentration of the delivered drug. These inputs can also be used to titrate the delivery of the medication to achieve a selected concentration of drug (e.g., in plasma, tissue, etc.). The drug sensors can be positioned on distal portions of the drug delivery device such as on the catheter or the outside of the porous chamber, or the as well as other sites in the body (e.g., a vein or artery) in order to develop a pharmacokinetic model of the distribution of the drug at multiple sites in the body. The apparatus can also include a sensor coupled to the controller which indicates when the medication pellets have been used up and/or exactly how many are left. The controller in turn can signal this data to an external communication device such as a cell phone, portable monitor or remote monitor (e.g., at the physician's office). In this way, the patient and/or medical care provider can take appropriate action before the apparatus runs out of medication.

The pellets or other solid form 100 of the medication are delivered to a delivery site such as the endocardial or epicardial surface of the heart where they are configured to be broken down, disintegrate and absorbed by body tissue fluids so as to produce a desired concentration of the drug at a target tissue site. In some applications, the delivery site can be the same as the target site, for example the heart. In other applications, the target site can be different from the delivery site, for example, the delivery site can be intramuscular tissue in the chest and the target site can be the heart or the liver. The delivery site can be adjacent the target site, for example adipose to deliver to underlying muscle tissue, or it can be placed at a non-oppositional site, for example, intramuscular delivery to reach the site of the heart. In each case, the medication pellet 100 can include a selected dose 100d of drug and be configured to disintegrate and be dissolved by body tissue fluids so as to yield a therapeutically effective concentration of the drug at the target tissue site such as the endocardial or epicardial surface of the heart. In many applications, this involves the pellet being dissolved by body tissue fluids at the delivery site (e.g., interstitial fluids bathing the pericardium or the blood bathing the endocardial or other portion of the myocardial wall) where the drug then diffuses into the myocardial wall. Accordingly, in these and other applications, the dose of the drug in the pellet can be titrated to achieve a selected concentration of the drug (or concentration range) for a selected period during and after dissolution of the pellet. Further, the dose of drug can be titrated to produce a desired therapeutic effect on the heart and/or cardiovascular system (e.g., treatment of arrhythmia, angina, myocardial infarction, congestive heart failure) while minimizing adverse reactions which may occur for larger doses of the drug when orally delivered. For example, in the case of sodium channel blockers for the treatment of arrhythmia (e.g., quinidine, procainamide and disopryamide), the dosage of drug can be titrated to prevent or reduce the severity or incidence of adverse reactions such as one or more of tachycardia, dry mouth, urinary retention, blurred vision and headache. In the case of cardiac glycosides for the treatment of arrhythmia (e.g., Digoxin or Digitoxin), the dosage of drug can be titrated to prevent or reduce the severity or incidence of adverse reactions such as atrial tachycardias, atrioventricular block and various forms of digitalis toxicity. Such titrations can be done using various dose response curve methods known in the art.

In some embodiments, the pellet 100 (including the drug dose) is configured to disintegrate and be dissolved by blood or tissue fluids which seep into the porous chamber. In particular embodiments for treating various cardiac rhythm disorders such as arrhythmia, the pellet is configured to rapidly disintegrate and be dissolved in blood or other fluid within the porous chamber. This can be achieved through the use of one or more super dis-integrants as well as disintegrating enhancing features (e.g., pores, cracks or other intrusions) in or one the pellet. It can also be achieved by treating the pellet prior or after delivery with mechanical, electromagnetic, acoustical or other energy to weaken the pellet structure, create cracks and other structural defects for the ingress of fluids or initiate the breakup of the pellet into smaller pieces.

In various applications, embodiments of the invention can be used to deliver solid form drugs to provide treatment for a number of medical conditions including coronary arrhythmia's (both atrial and ventricular including fibrillation), coronary ischemia (e.g., from a narrowed or blocked artery including that resulting in a heart attack), cerebral ischemia, stroke, anemia or other like condition. The apparatus can be implanted at or near the target tissue site (e.g., the heart) or at remote delivery site (e.g., intramuscularly in the chest or thigh.

In exemplary embodiments of methods for using the invention to treat a heart condition, for example cardiac arrhythmia, the apparatus can be implanted in the patient's chest to deliver drug to a delivery site DS within or near the heart. In specific embodiments, the drug storage device may be placed in the pectorial region while the distal end of the delivery member can be positioned on or near a surface of the heart, either the epicardial or endocardial surface. For embodiments where the apparatus is used to deliver drug to the myocardial wall, the lead and porous chamber can be fixed to the endocardial or epicardial wall using the corkscrew fixation element or other fixation device. Implantation can be done using an open or minimally invasive surgical procedure, for example, via percutaneous access through the vascular system. Prior to implantation, the drug reservoir can be loaded with a selected number of pellets to provide for delivery of pellets to the delivery site over an extended period of time, e.g., years. Once implanted, the pellets can be stored in the apparatus for an extended period of years (e.g., 1, 2, 5 or longer) without degradation or deleterious effect to the pellets (e.g., loss of drug potentcy or therapeutic effectiveness). The apparatus can deliver solid form medication to the delivery site at regular intervals (e.g., once a day, week, month, etc.) or in response to an input from a sensor. In the latter case, the input can be indicative of a particular medical condition or event such as an episode of arrhythmia. Embodiments of the controller described herein can be used to determine when to initiate delivery based on the sensor input and/or the time intervals for delivery for embodiments employing delivery at regular intervals. In either case, the controller can send a signal to the drug storage device. There it disintegrates/degrades and is dissolved in local tissue fluids to treat a local target tissue site (e.g., it dissolves in the interstitial fluids bathing pericardium to treat the heart or the CSF fluid to treat the brain), or it is subsequently absorbed into the blood stream where it is carried to a remote target tissue site (e.g., the liver, heart, etc.) or both. Further, pellets can be delivered based on input from a sensor providing physiologic data predictive of the medical condition (e.g., blood glucose) or another sensor that is configured to sense the local and/or plasma concentration of the drug. In some embodiments, pellet delivery can be controlled by sensing the state of disintegration of previously delivered pellets. For example, another pellet can be delivered when it has been determined that the previous pellet is in a particular state of disintegration (e.g., it has been completely or substantially disintegrated). This can be achieved by sending and receiving a signal from the pellet such as an optical, ultrasound or electrical signal. For example, for the use of optical signal reflectance measurements can be used to determine the state of disintegration. A particular disintegration state can be determined when the reflectance signal falls below a particular threshold. Similar approaches can be used for use of reflected ultrasound or impedance. The pellet can even include various echogenic, or optically opaque or other agents to enhance the reflected ultrasonic, optical or other signal. The pellet may also include various optical indicia having one or more of a pattern, size or shape configured to provide an indication of the state of disintegration of the pellet.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be sized and otherwise adapted for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for delivery of medication to a delivery site within the body of a patient, the apparatus comprising:
a drug storage device configured to be implanted within the patient's body, the storage device configured to store a plurality of solid form medication elements, each medication element comprising a drug;
a flexible delivery member having a proximal and distal end, the proximal end coupled to the drug storage device, the delivery member including a lumen for advancement of the medication element through the delivery member;
an advancement member configured to advance the medication element through the delivery member lumen; and
a capture chamber coupled to the distal end of the delivery member; the capture chamber including a housing having an interior volume for receiving the medication element, the housing including at least one porous section allowing tissue fluids to enter and exit the chamber; wherein the chamber is configured to i) retain a medication element received from the delivery member; ii) dissolve the medication element in tissue fluids within the interior volume to form a drug solution; and iii) deliver the dissolved drug through the at least one porous section to the delivery site.

2. The apparatus of claim 1, wherein the least one porous section comprises a polymer material.

3. The apparatus of claim 1, wherein medication element comprises a medication pellet.

4. The apparatus of claim 1, wherein the at least one porous section includes a tissue contacting porous section configured to contact tissue so as to deliver the drug solution to the delivery site.

5. The apparatus of claim 4, wherein the least one porous section further comprises a non-tissue contacting porous section.

6. The apparatus of claim 5, wherein the tissue contacting porous section has a first porosity and the non-tissue contacting porous section has a second porosity.

7. The apparatus of claim 4, wherein the tissue contacting section is configured to contact a surface of a heart.

8. The apparatus of claim 7, wherein the heart surface comprises an endocardial surface and the tissue fluid comprises blood.

9. The apparatus of claim 7, wherein the heart surface comprises an epicardial surface and the tissue fluid comprises interstitial fluid.

10. The apparatus of claim 7, wherein the heart surface is an atrial surface of the heart.

11. The apparatus of claim 7, wherein the tissue contacting surface is configured to bend and flex so as to not impede a wall motion of a beating heart.

12. The apparatus of claim 7, where in the capture chamber is configured to not impede a wall motion of a beating heart.

13. The apparatus of claim 12, wherein the capture chamber has at least one of a contour, flexibility or mass configured to not impede a wall motion of a beating heart.

14. The apparatus of claim 7, wherein the capture chamber has a contour configured to not impede blood flow through a chamber of the heart in which the capture chamber is placed.

15. The apparatus of claim 1, wherein the advancement member comprises a metal wire.

16. The apparatus of claim 1, wherein the advancement member has a ball shaped tip configured to engage the medication element.

17. The apparatus of claim 1, wherein the advancement member has a tip configured to sense contact with the medication element.

18. The apparatus of claim 17, wherein the advancement member tip is configured to sense contact with the medication element by a change in capacitance of at least one of the advancement member or advancement member tip.

19. The apparatus of claim 1, wherein the advancement member has a wound state when not advanced and an unwound state when advanced.

20. The apparatus of claim 1, further comprising a drive means coupled to the advancement member for advancing the advancement member.

21. The apparatus of claim 20, the drive means comprises at least one of pinch rollers or an electric motor.

22. The apparatus of claim 1, where the capture chamber includes a fixation device for fixing the capture chamber to a tissue surface.

23. The apparatus of claim 22, wherein the fixation device is configured to be fixed to a heart surface.

24. The apparatus of claim 23, the fixation device comprises a shaped coil, a helical-shaped coil or a metal helical shaped coil.

25. The apparatus of claim 23 wherein the fixation device is configured to be fixed to an endocardial surface of the heart.

26. The apparatus of claim 23, wherein the fixation device is configured to function as an electrode to sense electrical activity of the heart or deliver an electrical signal to the heart.

27. The apparatus of claim 26, wherein the fixation device is electrically coupled to at least one electrical lead.

28. The apparatus of claim 27, wherein the at least one electrical lead is electrically coupled to at least one of an electrically stimulator or a pace making device.

29. The apparatus of claim 27, wherein the at least one lead comprises a least a first and a second lead.

30. The apparatus of claim 29, wherein the delivery member comprises an inner and an outer delivery member and a portion of a length of the least one lead is positioned between the first and the second delivery member.

31. The apparatus of claim 1, wherein the delivery member comprises a catheter.

32. The apparatus of claim 1, wherein the drug delivery lumen includes a reinforcing metal coil configured to provide torsional support to the lumen to maintain a patentcy of the lumen when the delivery member is bent or crimped.

33. The apparatus of claim 1, further comprising a resealable septum coupled to the distal end of the delivery member, the septum configured to open to allow passage of the medication element into the capture chamber and then close to prevent ingress of fluids into the delivery member.

34. The apparatus of claim 33, wherein the septum includes a resealable slit for passage of the medication element.

35. An apparatus for drug delivery to a patient's heart, the apparatus comprising:
   a drug storage device configured to be implanted within the patient's body, the storage device configured to store a plurality of medication elements each medication element comprising at least one drug;
   a flexible delivery member having a proximal and distal end, the proximal end coupled to the drug storage device, the delivery member including a lumen for advancement of the medication element through the delivery member;
   an advancement member configured to advance the medication element through the delivery member lumen; and
   a capture chamber coupled to the distal end of the delivery member; the capture chamber including a housing having an interior volume for receiving the medication element, the housing including at least one porous section allowing tissue fluids to enter and exit the chamber; wherein the chamber is configured to i) retain a medication element received from the delivery member; ii) dissolve the medication element in tissue fluids within the interior volume to form a drug solution; and iii) deliver the dissolved drug through the at least one porous section to a myocardial delivery site; at least a portion of the porous section configured to be positioned on a surface of the heart wall.

36. The apparatus of claim 35, wherein the heart wall surface comprises an endocardial surface and the tissue fluid comprises blood.

37. The apparatus of claim 35, further comprising a fixation device for fixing the capture chamber to the hear wall surface.

38. An apparatus for delivery of medication to a delivery site within the body of a patient, the apparatus comprising:
   a drug storage device configured to be implanted within the patient's body, the storage device configured to store a plurality of solid form medication elements, each medication element comprising a drug;
   a flexible delivery member having a proximal and distal end, the proximal end coupled to the drug storage device, the delivery member including a lumen for advancement of the medication element through the delivery member;

an advancement member configured to advance the medication element through the delivery member lumen; and a capture chamber coupled to the distal end of the delivery member; the capture chamber including a housing having an interior volume for receiving the medication element, the housing including at least one porous section allowing tissue fluids to enter and exit the chamber; the at least one porous section including a tissue contacting porous section configured to contact tissue so as to deliver the drug solution to the delivery site; and wherein the capture chamber is configured to: i) retain a medication element received from the delivery member; ii) dissolve the medication element in tissue fluids within the interior volume to form a drug solution; and iii) deliver the dissolved drug through the tissue contacting porous section to the delivery site.

39. An apparatus for drug delivery to a patient's heart, the apparatus comprising:

a drug storage device configured to be implanted within the patient's body, the storage device configured to store a plurality of medication elements each medication element comprising at least one drug;

a flexible delivery member having a proximal and distal end, the proximal end coupled to the drug storage device, the delivery member including a lumen for advancement of the medication element through the delivery member;

an advancement member configured to advance the medication element through the delivery member lumen; and a capture chamber coupled to the distal end of the delivery member; the capture chamber including a housing having an interior volume for receiving the medication element, the housing including at least one porous section allowing tissue fluids to enter and exit the chamber; wherein the chamber is configured to: i) retain a medication element received from the delivery member; ii) dissolve the medication element in tissue fluids within the interior volume to form a drug solution; and iii) deliver the dissolved drug through the at least one porous section to a myocardial delivery site; at least a portion of the porous section configured to be positioned on a surface of the heart wall to deliver the dissolved drug to the myocardial delivery site without impeding motion of the heart wall.

40. The apparatus of claim 39, wherein the tissue contacting surface is configured to bend and flex so as to not impede a wall motion of a beating heart.

41. The apparatus of claim 39, wherein the capture chamber has at least one of a contour, flexibility or mass configured to not impede a wall motion of a beating heart.

* * * * *